(12) United States Patent
Collins et al.

(10) Patent No.: US 8,951,614 B2
(45) Date of Patent: Feb. 10, 2015

(54) MECHANISM FOR COATING LABORATORY MEDIA WITH PHOTO-SENSITIVE MATERIAL

(75) Inventors: Mark Andrew Collins, Dripping Springs, TX (US); Charles W. Morrison, Jarrell, TX (US)

(73) Assignee: Vaporprint, LLC, Morrison, CO (US)

( * ) Notice: Subject to any disclaimer, the term of this patent is extended or adjusted under 35 U.S.C. 154(b) by 195 days.

(21) Appl. No.: 13/092,728

(22) Filed: Apr. 22, 2011

(65) Prior Publication Data

US 2012/0268547 A1    Oct. 25, 2012

(51) Int. Cl.
| | |
|---|---|
| B41J 2/385 | (2006.01) |
| B41J 2/435 | (2006.01) |
| B05D 3/00 | (2006.01) |
| G01N 1/28 | (2006.01) |
| C08F 2/46 | (2006.01) |
| C08J 7/04 | (2006.01) |
| C08J 7/18 | (2006.01) |
| H05B 6/64 | (2006.01) |
| G06K 1/12 | (2006.01) |
| G01N 35/00 | (2006.01) |

(52) U.S. Cl.
CPC .......... *G06K 1/126* (2013.01); *G01N 35/00732* (2013.01); *G01N 2035/00861* (2013.01)
USPC .......... 427/510; 347/139; 347/153; 347/262; 427/2.11; 427/492; 427/521

(58) Field of Classification Search
USPC ......... 347/138, 153, 262; 427/2.11, 492, 510, 427/521
See application file for complete search history.

(56) References Cited

U.S. PATENT DOCUMENTS

| | | | |
|---|---|---|---|
| 2007/0098900 A1* | 5/2007 | Abe et al. | 427/261 |
| 2008/0056951 A1* | 3/2008 | Angros | 422/99 |
| 2009/0003151 A1* | 1/2009 | Honda et al. | 369/44.27 |

* cited by examiner

*Primary Examiner* — Justin Seo
*Assistant Examiner* — Kendrick Liu
(74) *Attorney, Agent, or Firm* — Blakely Sokoloff Taylor & Zafman

(57) ABSTRACT

A method for coating a laboratory print media with a photo-sensitive material may include generating, at a printer, a request to label a laboratory media. The laboratory media includes applying multiple coating layers to a laboratory print media to produce a human-readable and machine-readable label within a dedicated area of the print media. The multiple coating layers include at least a material based on photo-sensitive ink that is thermally-activated, and protected by a chemical and physical protective barrier/layer. The method may further include generating, using a printing mechanism, an image within the dedicated area of the print media. The image includes a laser-based image reflecting off of the photo-sensitive ink.

20 Claims, 5 Drawing Sheets

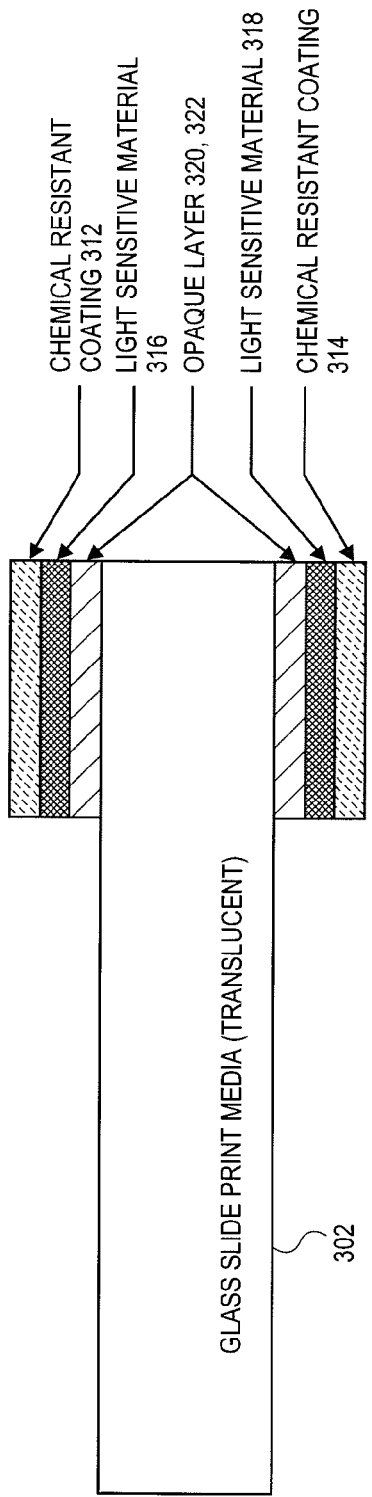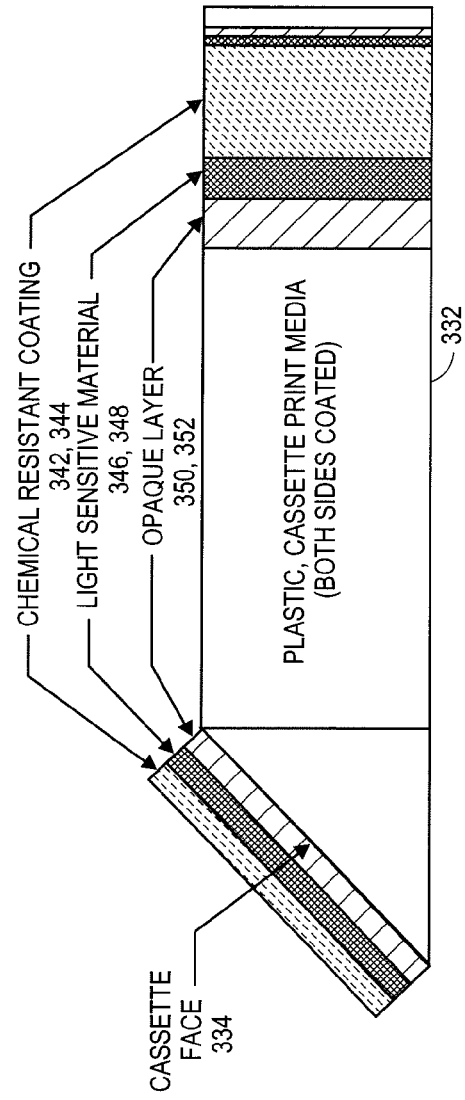

MECHANISM FOR COATING LABORATORY MEDIA WITH PHOTO-SENSITIVE MATERIAL

RELATED APPLICATIONS

The present application is related to co-filed U.S. patent application Ser. No. 13/092,687 entitled "Mechanism for Labeling Laboratory Print Media" and U.S. patent application Ser. No. 13/092,749 entitled "Mechanism for Remotely Facilitating Authorization and Activation of Laboratory Print Media Labeling", which are assigned to the assignee of the present application

TECHNICAL FIELD

The embodiments of the invention relate generally to media printing and, more specifically, relate to providing a mechanism for coating laboratory media with photo-sensitive material.

BACKGROUND

Good Laboratory Practices (GLP) standards dictate that medical or laboratory samples (e.g., histologic specimen, such as microscopic anatomy of cells and tissues of plants, animals, and humans) are to be identified and their medical containers or laboratory print media (herein referred to as "print media", "media", "media containers", or "media supplies") (e.g., slides, cassettes, test tubes, flasks, etc.) be labeled as soon as a sample enters a medical laboratory in order to identify and track the sample and to reduce any potential errors caused by improper identification of the sample. To address these concerns, special laboratory printers (or simply referred to as "printers") were developed. Laboratory printers are commonly used to print laboratory media with certain identifying information. Typically, once a media has been printed with a label, the sample contained on or within the media can be tracked throughout the process within the laboratory.

To further enhance laboratory efficiency, software applications and systems (e.g., Laboratory Information System (LIS), Laboratory Integration Management Solution or Laboratory Information Management System (LIMS), etc.) were developed to be used to reliably identify and track samples as they are introduced into laboratories. LIS refers to a software system that can be used to receive, process, and store information generated by laboratory processes. LIMS refers to a software or database system that is used to integrate laboratory software and instruments, manage laboratory samples, standards, users, etc., in guiding laboratory samples through laboratories based on a set of defined processes or workflows for quality control in testing these samples. Since LIMS can facilitate simultaneous tracking of thousands of samples, there remains the need for accurate identification of each sample and the media that holds it.

It is important to accurately maintain the specimen sample and print media identification because any inaccuracy (such as due to a faded label) could lead to potential mismatch and subsequent problems. One reason these identification/information labels are difficult to accurately maintain is that the print media typically goes through various testing processes, including chemical and mechanical processes, which can easily distort these identification labels to the extent that some or all of the information becomes illegible. It is important to provide human- and/or machine-readable identification that remains on the print media regardless of the laboratory processes and chemicals it encounters.

Current laboratory printing technologies for conventional laboratory printers include ink-jet and ribbon printers. One problem with the laboratory ink-jet printers is that they require using a special ink that is ultraviolet (UV) sensitive that can be cured so that any chemicals used in the sample diagnosis process do not accidentally remove the printed label from the media. However, each time a UV light bulb (that is required to cure the special ink) goes out (typically, without a warning), it carries the potential to contaminate hundreds of samples and render them unable to be tracked in the LIMS, by way of the uncured UV sensitive ink. Ribbon printers require that a user correctly and cautiously load a ribbon into a ribbon printer without damaging or wasting too much of the ribbon. Further, instead of pre-loading laboratory media into ribbon printers for automatic printing, a user is required to load the media and continue watching the printer ribbon to be sure that the ribbon does not run to the end and stop all media printing processes.

Other conventional limitations include requiring laser toner cartridges, coating the media in black ink that is ablated or removed to create the label image, needing vacuum filters for laser ablative printers, which can be "scratched off" since the laser ablative process actually removes ink from the existing print media.

SUMMARY

In accordance with embodiments, there are provided methods, apparatus, and systems for coating print media with photo-sensitive material, such as a method of embodiments includes coating a laboratory print media with a photo-sensitive material may include generating, at a printer, a request to label a laboratory media. The laboratory media includes applying multiple coating layers to a laboratory print media to produce a human-readable and machine-readable label within a dedicated area of the print media. The multiple coating layers include at least a material based on photo-sensitive ink that is thermally-activated, and protected by a chemical and physical protective barrier/layer. The method may further include generating, using a printing mechanism, an image within the dedicated area of the print media. The image includes a laser-based image reflecting off of the photo-sensitive ink.

BRIEF DESCRIPTION OF THE DRAWINGS

The invention will be understood more fully from the detailed description given below and from the accompanying drawings of various embodiments of the invention. The drawings, however, should not be taken to limit the invention to the specific embodiments, but are for explanation and understanding only.

FIGS. 3A and 3B illustrate multiple coating layers placed on a print media according to one embodiment of the invention;

DETAIL DESCRIPTION

Figure 1:
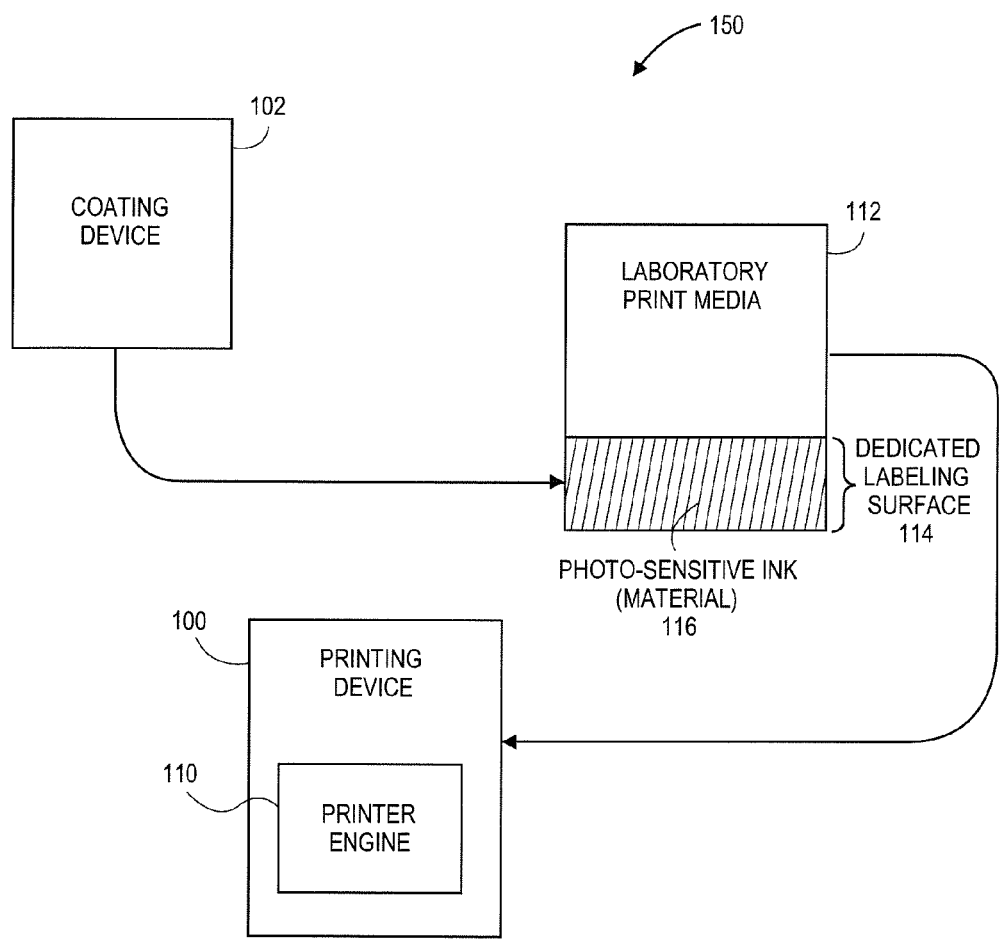
FIG. 1 illustrates a photo-sensitive material-based coating mechanism for coating and processing a laboratory print media according to one embodiment of the invention.

Embodiments of the invention providing a mechanism for coating print media with photo-sensitive material are described. A method of embodiments includes coating a laboratory print media with a photo-sensitive material may include generating, at a printer, a request to label a laboratory media. The laboratory media including applying multiple coating layers to a laboratory print media to produce a human-readable and machine-readable label within a dedicated area of the print media. The multiple coating layers include at least a photo-sensitive material based on photo-sensitive ink that is thermally-activated. The method may further include generating, using a printing mechanism, an image within the dedicated area of the print media. The image includes a laser-based image reflecting off of the photo-sensitive ink.

The embodiments of the present invention are provided for printing of laboratory print media for identifying samples or specimen (e.g., histological specimen, such as microscopic anatomy of cells and tissues of plants, animals, and humans) and their print media (e.g., laboratory media containers, such as cassettes, slides, test tubes, flasks, etc.) within a laboratory environment by providing a mechanism for coating laboratory media using a light- or photo-sensitive material (e.g., photo-sensitive ink that is thermally-activated). This technique allows the generally-translucent media to be used in existing laboratories employing various printing methods, such as ink-jet printers, ribbon printers, thermal transfer, laser toner, laser ablative processes, and the like. This way, in one embodiment, a laboratory can use one type of print media that covers all types of printers, i.e., it does not impede any of the existing printing technologies, such as ink-jet printers, ribbon printers, laser printers, and the like. In one embodiment, the novel photo-sensitive ink is introduced and used to provide the photo-sensitive material-based coating of the print media. This photo-sensitive ink is compatible with all existing printing technologies and is economical and beneficial over existing printing technologies by reducing the number of consumables (e.g., ultra-violet (UV) curable ink, UV bulbs to cure the ink, printer ribbons, laser toner cartridges, etc.) that are required to enable various existing printing processes. Further, the embodiments of the present invention provide for print media labeling using the photo-sensitive ink that is faster, more efficient, Eco-Green, and more technologically-mature than the conventional print media labeling. With regard to the embodiments of the present invention, throughout this document, the terms "labeling", "printing", and "imaging" are used interchangeably and synonymously; similarly, terms like "label", "print" and "image" are also synonymously and interchangeably used as are the terms "light", "thermal", and "photo".

Labeling of laboratory print media refers to producing an image on the print media such that the image includes a relevant human- and machine-readable image having certain identifying information (e.g., specimen-, media- or patient-related information, etc.) that can be used to identify and track various specimen samples contained within or on the print media during the samples' processing (e.g., diagnosis, sample testing including chemical and/or mechanical processes, etc.) within the laboratory environment. In one embodiment, the image may be produced by inducing a visible color change on the print media using a laser on the laser-sensitive material on the surface of the print media (e.g., on a dedicated portion of the surface of the print media). For example, and in one embodiment, a laser light source, such as a laser, may be used to generate a laser light beam, a moving reflective device (e.g., mirror), and a fixed print media surface coated with light- or photo-sensitive material. For example, a light beam may be adapted to activate the photo-sensitive labeling layer or coating on the print media to produce visible change on the print media surface from translucent to opaque to form a human- and machine-readable image on the print media.

FIG. 1 illustrates a photo-sensitive material-based coating mechanism 150 for coating and processing a laboratory print media 112 according to one embodiment of the invention. Photo-sensitive ink-based coating mechanism 150 ("mechanism") refers to a high-level process for coating a print media 112 (e.g., cassettes, slides, test tubes, flasks, etc.) with a novel photo-sensitive material that includes a novel photo-sensitive ink 116 (also herein referred to as "light-sensitive ink" or "thermal-sensitive ink" or simply "ink") that is light- or thermal- or photo-activated. In one embodiment, a particular area 114 of the print media 112 that is dedicated for printing labels and therefore is used for coating with the photo-sensitive ink 116 using a coating device 102. The particular area 114 is herein referred to as "dedicated or designated labeling surface", "dedicated or designated coating surface", or simply "surface", etc. In one embodiment, the coating device 102 may include, but is not limited to, a sprayer to spray the photo-sensitive ink 116 on the dedicated labeling surface 114 of the print media 112, a roller to roll the ink 116 on the print media 112, or a mechanical device (e.g., a robotic hand) to dip the surface 114 of the print media 112 into a pool of ink 116 contained in a beaker, or the like. It is contemplated that the surface 114 is only shown here as an example for brevity and simplicity and that it can significantly vary in terms of its size, location, etc., depending on the type and nature of the print media 112, such as a cassette as opposed to a slide, and the like.

In one embodiment, the ink 116 can be coated on the print media 112 at any time after the print media 112 has been manufactured, such as by the manufacturer, by sending the print media 112 to a coating company that performs print media coating, or the like. In any case, the print media 112 is coated with the ink 116 prior to the print media 112 being exposed to a printing device 100. Again, as with other examples in this document, printing device 100 is merely used here as an example for brevity and simplicity and ease of understanding and it is contemplated that the ink 116 and the ink-coated print media 112 can be used with any number of printing devices, such as the printing device 100 having a laser-based print capabilities provided by the printer engine 110.

In the illustrated mechanism 150, the print media 112 with its designated labeling area 114 coated with the ink 116 is inserted into the printing device 100 for printing purposes where the printer engine 110 facilitates "lasing" of the surface 114 of the print media 112 to produce a laser-based label or image that is produced through and protected by (a seal coat layer of) the ink 116. As will be described subsequently, in one embodiment, the surface 114 may be coated with multiple layers, such as (1) a reflective layer (which includes, for example, the white print area of a slide or the color area of plastic of a cassette) that is used to reflect, for example, the laser light (of a laser associated with the printer engine 110) onto a photo-sensitive layer, (2) the photo-sensitive layer is made with a photo-sensitive material, such as the photo-sensitive ink 116, that is light or thermal or photo activated, and (3) a seal coat layer that ensures that the ink 116 is impervious to any of the chemicals used during laboratory processes within a laboratory environment so that the image or label cannot be scratched or faded off of the print media 112.

Printing device 100 may serve as a printer that includes a base computing/printing platform employing a combination of hardware and software. The base platform may include an operating system serving as an interface between any hardware or physical resources of the printing device 100 and a user (e.g., an end-user, such as a laboratory technician or assistant, using the printing device 100 to label the print media 112). In some embodiments, the base platform may further include processors, memory devices, network devices, printer and other drivers, or the like. Memory devices and/or database (e.g., a remote or local storage medium) may be used to store printing system software, printer-, print media-, specimen-, and/or patient-specific data files, etc. It is contemplated that the printing device 100 may include various computing features or be part of a computing machine. Terms like "machine", "device", "computer" and "computing system" are used interchangeably and synonymously throughout this document. As illustrated, the printing device 100 employs a printer engine 110 that includes a mechanism for laser-based labeling of the print media 112.

In one embodiment, the photo-sensitive ink-coated print media 112 is inserted into the printing device 100 through a staging area (e.g., tube, flatbed, hopper, slot, etc.) to be labeled using the printer engine 110. The printer engine 110 may contain various hardware and/or software labeling components and entities to facilitate laser-based media labeling of the print media 112, such as producing laser-based images on the surface 114 of the print media 112 by having a laser beam sufficiently articulated across the entire surface of the print media 112 and forming an image within the dedicated labeling surface 114. A user (e.g., an end-user, such as a lab assistant or technician, etc.) may, in one embodiment, may place the print media 112 into the printing device 100 and may have direct access to the printing device 100 (e.g., using a touch screen display of the printing device 100 without the use of a dedicated computer operator) or, in another embodiment, through a computing device in communication with the printing device 100.

In one embodiment, the photo-sensitive ink- and laser-based imaging of the print media is technologically advanced, environmentally friendly, and fully protected against fading or scratching during subsequent handling of the print media 112 during various chemical and/or mechanical processes within the laboratory environment. It is contemplated that the laser-based printing is merely used here as an example for brevity and ease of understanding and that the embodiments of the invention are fully and equally applicable to other types of print media imaging and printing devices (e.g., ribbon printers, ink-jet printers, etc.).

Figure 2A:
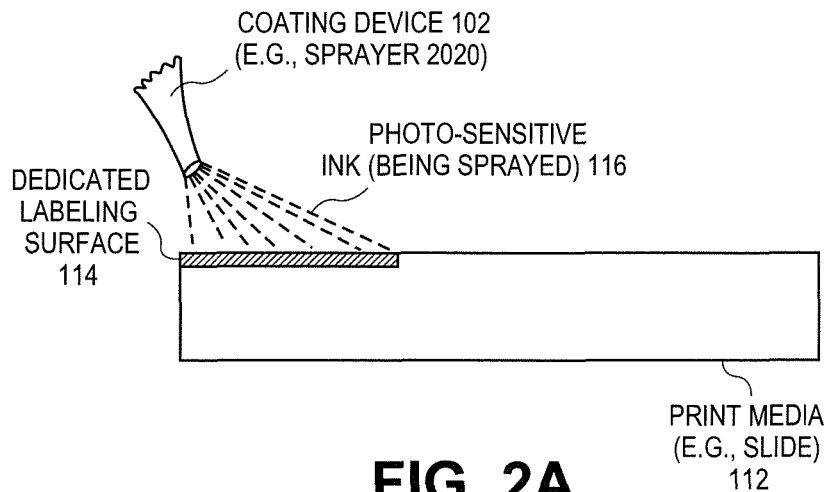
FIG. 2A thru 2C illustrate coating devices to coat a photo-sensitive material on laboratory print media according to one embodiment of the invention.
Figure 2B:
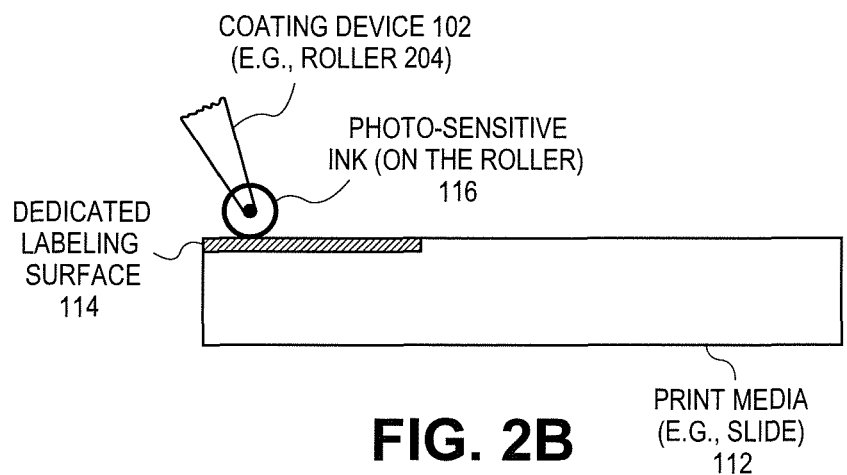
Figure 2C:
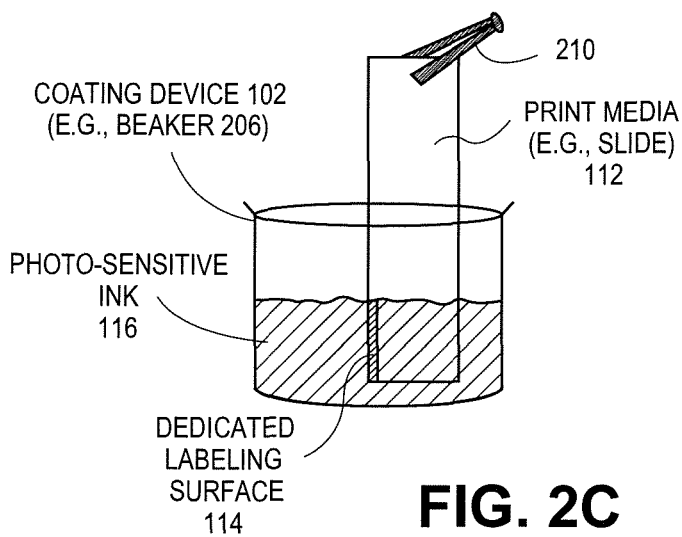

FIGS. 2A-2C illustrate coating devices 102 to coat a photo-sensitive material on laboratory print media 112 according to one embodiment of the invention. Print media 112 may be coated with the photo-sensitive material, including a photo-sensitive ink 116, at a manufacturing facility after the print media 112 has been manufactured or sent to an independent coating facility that is separate from the manufacturing facility, or the like. As previously referenced in FIG. 1, a coating device 102 may include any number of coating devices 202-206 for applying the photo-sensitive ink 116 on the print media 112 (e.g., slide) using a variety of different methods (e.g., depending on the type of print media 112 being used and the amount of dots per inch (dpi) to be created on the print media 112, as desired or necessitated). As illustrated in FIG. 2A, a coating device 102 includes a sprayer 202 that sprays the photo-sensitive ink 116 on the dedicated labeling surface 114 of the print media 112. Since spraying includes much finer coating, the ink 116 when sprayed on the print media 112 can achieve a relatively finer dpi along with an appropriate wavelength.

FIG. 2B illustrates a roller 204 as a coating device 102 to roll the photo-sensitive ink 116 on the dedicated labeling surface 114 of the print media 112 (e.g., slide). For example, the roller may be separately dipped into the ink 116 and then rolled over the surface 114 to deposit the ink 116 on the surface 114 of the print media 112.

FIG. 2C illustrates a container 206 (e.g., a beaker) as a coating device 102 that contains the photo-sensitive ink 116. In this embodiment, the print media 112 (e.g., slide) may itself be dipped into the container 206 such that to capture the photo-sensitive ink 116 on the dedicated labeling surface 114 of the print media 112. It is contemplated that dipping could cause some smudging if too much ink 116 gets on the surface 114 when the print media 112 is not properly dipped, etc., and therefore, dipping could be performed using an automated mechanical device 210 (e.g., a robotic hand) that is programmed to properly dip the print media 112 into the ink 116 such that only an appropriate amount of the ink 116 gets on the surface 114 of the print media 112. Similarly, in one embodiment, the sprayer 202 and the roller 204 can be attached to a machine to perform the spraying and rolling of the ink 116, respectively, to place or deposit the appropriate amount of the ink 116 on the surface 114. It is contemplated that other types and number of coating devices 102 may be employed for coating the ink 116 on any type of print media (e.g., cassettes, test tubes, flasks, etc.).

FIGS. 3A and 3B illustrate multiple coating layers placed on a print media according to one embodiment of the invention. Referring to FIG. 3A, a side view of a translucent print media, such as a media slide 302, is illustrated having multiple coating layers, such as a set of chemical resistant coating layers 312, 314, a set of photo-sensitive material layers 316, 318, and a set of opaque layers 320, 322. Since the media slide 302 is generally made with glass, one or more opaque layers 320, 322 may be provided as a colored print area of the dedicated label surface to allow a user (e.g., a laboratory assistant or technician) to hand write or print certain identifying information (e.g., sample-specific identification, patient-specific identification, etc.) using various types of print processes (e.g., laser printing, ribbon printing, ink-jet printing, etc.). Next to or on top of the opaque layer 320, 322 is placed a photo-sensitive material layer 316, 318 that is generated using a photo-sensitive material, such as the aforementioned photo-sensitive ink.

Similarly, now referring to FIG. 3B, a side view of another print media, such as a media cassette 332, is illustrated along with multiple coating layers, such as a set of chemical resistant coating layers 342, 344, a set of light sensitive material layers 346, 348, and a set of opaque layers 350, 352. The opaque layers 350, 352 of the media cassette 332 represent reflective opaque layers that may be colored layers for writing or printing identification information using various types of print processes (e.g., laser printing, ribbon printing, ink-jet printing, etc.). Typically, the media cassette 332 is less likely to have opaque layers 350, 352 (like those of the media slide 302) since the media cassette 332 is generally made with plastic and not glass and is therefore not translucent like the media slide 302; therefore, the media cassette 332 may have one or more reflective opaque layer 350, 352 already on them. It is contemplated that there may be other media cassettes that are made with clear glass and in such cases, reflective opaque layers 350, 352 may be first applied on them (as is done with the media slide 302) for imaging and before other layers, such as the photo-sensitive material layers 346, 348 made of the photo-sensitive ink, and chemical resistant coating layers 342, 344, are applied. The chemical resistant coating layers 312, 314 and 342, 344 are applied to protect the image on the print media slide 302 and cassette 334 so that the label or image can be preserved despite the subsequent handling of the print media 302, 332 during laboratory processing which, as previously mentioned, includes exposure to various chemicals, human touching, mechanical processes, etc.

Figure 4:
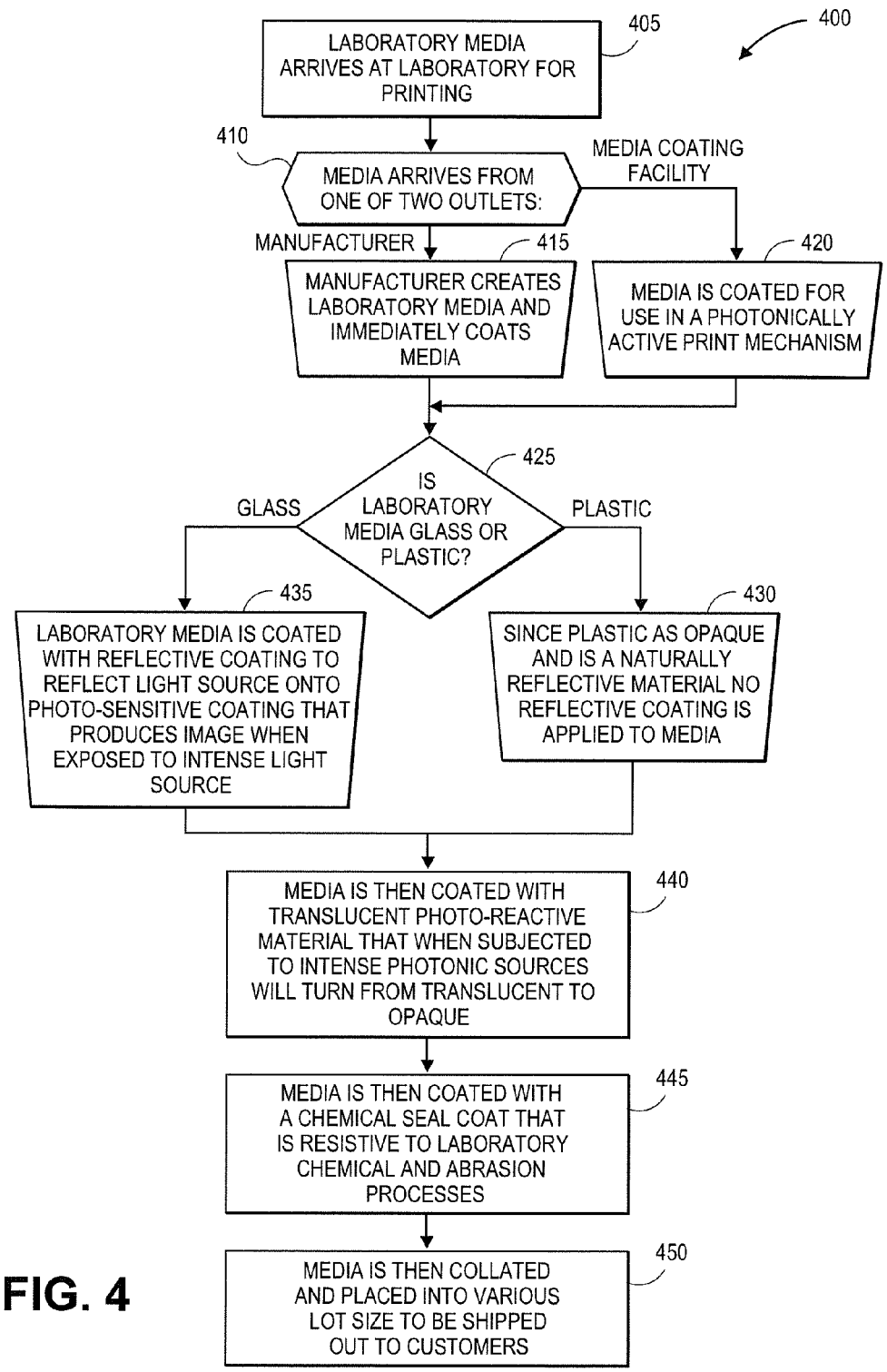
FIG. 4 illustrates a method for coating laboratory print media with a photo-sensitive material according to one embodiment of the invention.

FIG. 4 illustrates a method 400 for coating laboratory print media with a photo-sensitive material according to one embodiment of the invention. Method 400 may be performed by processing logic that may comprise hardware (e.g., circuitry, dedicated logic, programmable logic, microcode, etc.), software (such as instructions run on a processing device), or a combination thereof, such as firmware or functional circuitry within hardware devices. In one embodiment, method 400 is performed by one or more coating devices of FIG. 1 along with a printing mechanism (such as FIG. 1's printing device employing a printer engine).

Method 400 begins at block 405 with a laboratory print media (e.g., slide, cassette, test tube, etc.) arriving at a laboratory for imaging or printing a label. At block 410, a determination is made as to the outlet or the source of the print media. If the print media source is its manufacturer, at block 415, the manufacturer, after the print media has been manufactured, performs coating of the print media with a photo-sensitive ink to generate the light sensitive material layer on the dedicated labeling surface of the print media. The manufacturer may also place an opaque layer and a chemical resistant coating layer on the print media. For example, in case of the print media being a slide made of clear glass, an opaque layer may be applied as a colored layer for writing, printing, or imaging of information (e.g., identification information) on to it by any number and types of printing mechanisms (e.g., laser, ribbon, inkjet, etc.). Since a typical cassette is made of plastic, it may already have an opaque layer serving the same purpose. The ink-based photo-sensitive material layer allows all existing printing techniques to work with the opaque layers to print an image on the dedicated labeling surface of a print media. The chemical resistant coating layer allows for preservation of that information on the opaque layer of the media so it is protected from fading or scratching against various subsequent chemical and/or mechanical laboratory processes.

As with the manufacturer, at block 420, the print media may be coated with the three layers mentioned above including the ink-based photo-sensitive material layer at a coating facility as opposed to at a manufacturer's facility. In other words, print media may be made at a manufacturer's facility and then sent to an independent coating facility (e.g., an independent company that specializes in coating print media) wherein the print media is coated for use on a photonically-active print mechanism.

At block 425, a determination is made as to whether the print media is made of glass (e.g., slide) or plastic (e.g., cassette). If the print media is made of plastic, at block 430, no reflective coating (e.g., opaque layer) is needed to be applied to the print media since plastic is a naturally reflective material. If, however, at block 435, the print media is made of glass, the print media may be coated with a reflective opaque coating to reflect light source onto the photo-sensitive coating (of the photo-sensitive ink) that produces a label or image when exposed to an intense light source.

At block 440, the print media is then coated with a translucent photo-reactive or photo-sensitive material, such as the photo-sensitive ink, that when subjected to intense photonic sources turns from being translucent to opaque. At block 445, the print media is then coated with a chemical seal coating that is resistive to laboratory chemical and abrasion processes. At block 450, the print media is then collated and placed into various lot sizes to be shipped out to various customers to be used in laboratories.

Figure 5:
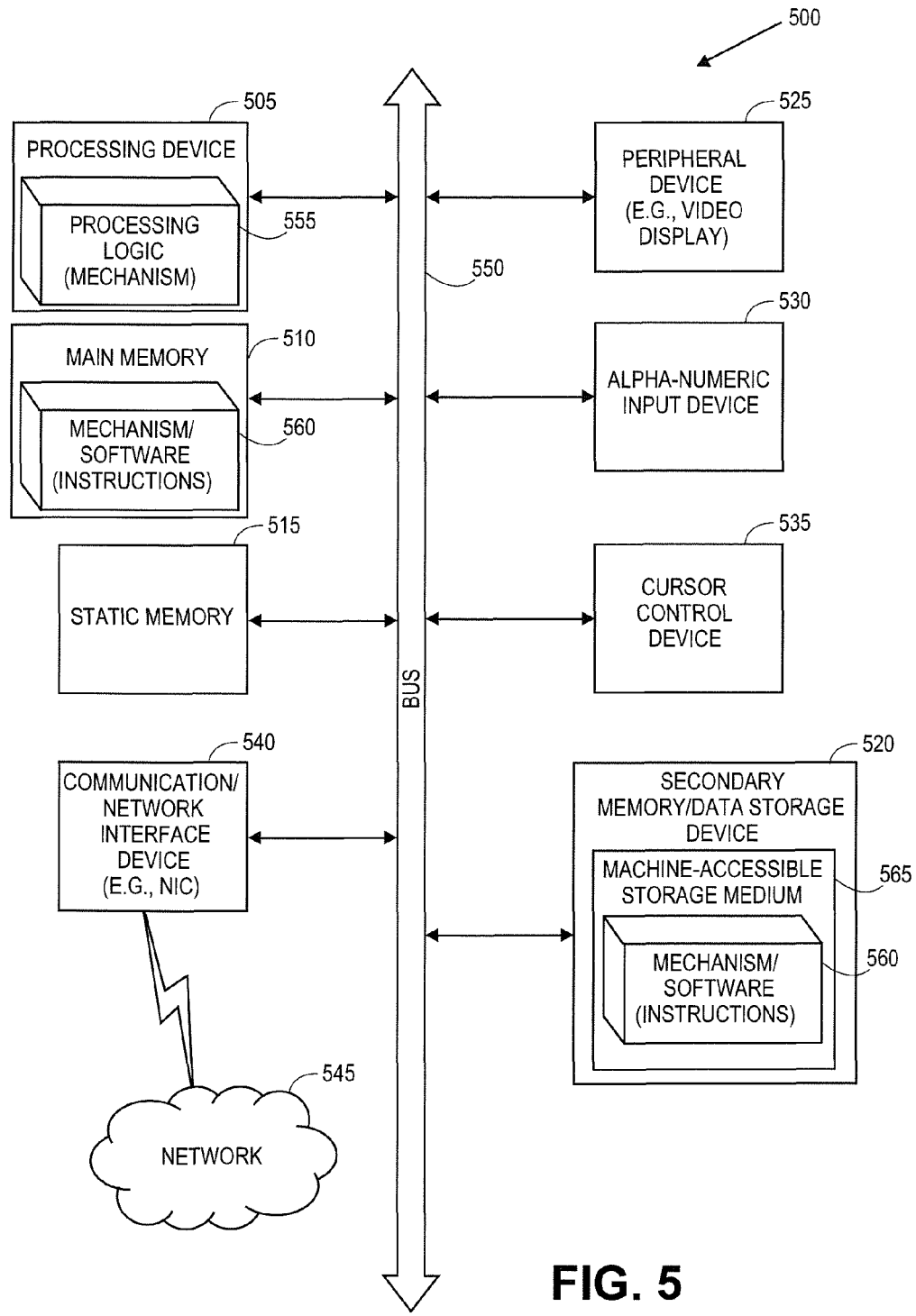
FIG. 5 illustrates a computer system according to one embodiment of the invention.

FIG. 5 illustrates a computer system for, for example, employing a printing mechanism having a printer engine or one or more coating devices of FIG. 1 according to one embodiment of the invention. As aforementioned, embodiments of the invention are applicable with any types of printing systems and techniques and thus the computer system 500 may be employed with any type of a printing system, such as FIG. 1's printing device having a printer engine. Computer system 500 represents or includes a basic circuitry to support FIG. 1's printing device employing a printer engine to perform various printing tasks of laboratory media in a laboratory environment. In one embodiment, computer system 500 provides the basic circuitry that is employed within the printer to represent the printer as a printing device or, in another embodiment, the computer system 500 may represent an outside-the-printer (local or remote) basic circuitry that is in communication with and facilitates the printer to perform its printing tasks. Computer system 500 may include and function in a server or client computer system capacity in, for example, a server-client environment. Computer system 500 include or represent or support a printer, such as the printing device of FIG. 1, a personal computer (PC), a Personal Digital Assistant (PDA), a computer pad or tablet, a smart mobile phone, a web server, or any data processing machine capable of storing and executing instructions to perform various tasks (including the ones performed by the printer engine of FIG. 1) mentioned throughout this document. In some embodiments, the computer system 500 may include or represent or be used to facilitate one or more of the coating devices (of FIG. 1) to facilitate coating of print media.

Although the computer system 500 shown as a single machine, it is contemplated that the term "machine", as referred to in this document, may include any number of machines in communication with each other or other remote machines. Computer system 500 may be in communication with other machines over a network (e.g., local area network (LAN), wide area network (WAN), metropolitan area network (MAN), intranet, the Internet, etc.) as connected or networked through a communication/network interface device 540 (e.g., network interface card, USB connection, modem, other devices such as to connect to Ethernet, token ring, etc.). Further, computer system 500 may be accessed by, or communicated with, using various other input/output (I/O) devices, such as an input device, such as an alpha-numeric input device 530 (e.g., keyboard) and/or a cursor control device 535 (e.g., mouse), and a peripheral display device 525 (e.g., a video display device, such as a liquid crystal display (LCD), a cathode ray tube (CRT), etc.) and other similar devices, such as speakers, microphones, etc., connected through a graphics port, chipset, or another human or machine interface device.

Computer system 500 includes a processing device 505. Processing device 505 represents one or more general-purpose processing devices (such as a microprocessor, central processing unit, etc.) and more particularly, the processing device may be complex instruction set computing (CISC) microprocessor, reduced instruction set computer (RISC) microprocessor, very long instruction word (VLIW) microprocessor, or a processing device implementing other instruction sets or a combination of instruction sets. Processing device 505 may also be one or more special-purpose processing devices (e.g., an application specific integrated circuit (ASIC), a field programmable gate array (FPGA), a digital signal processor (DSP), a microprocessor, a network processor, etc.). In one embodiment, processing device 505 is configured to execute the processing logic 455 (e.g., printer engine processing logic) for performing the operations and methods discussed herein and as performed by the printer engine of FIG. 1.

Computer system 500 further includes a main memory 510 (e.g., read-only memory (ROM), flash memory, random access memory (RAM), dynamic RAM (DRAM), synchronous DRAM (SDRAM), etc.), a static memory 515 (e.g., flash memory, static random access memory (SRAM), etc.), and other storage devices 520 (e.g., a data storage device or a magnetic disk or optical disc in the form of a drive unit, which may include fixed or removable machine-accessible or computer-readable storage medium), which communicate with each other via a bus 450. Storage 520 may include a non-transitory machine-accessible storage medium 565 that may then be used to store one or more sets of instructions 560 (e.g., printer engine instructions). These instructions 560 may be transmitted or received over a network via the network interface device 540 coupled with a network 545 (e.g., Internet). The instructions 560 of the printer engine of FIG. 1 may also reside, completely or at least partially, within the main memory 510 and/or within the processing device 505 as processing logic 555 (e.g., printer engine processing logic) during execution thereof by the computer system 500, the main memory 510 and the processing device 505 also constituting a non-transitory machine-readable storage media. Further, in one embodiment, the printing mechanism, the printing device, the printer engine, or the coating mechanism of FIG. 1 may be employed (entirely) on a single machine, such as computer system 500, or (partially or entirely) on different computer systems.

While the non-transitory machine-accessible storage medium 565 is described as a single medium, the term "machine-accessible storage medium" should be taken to include a single medium or multiple media (e.g., a centralized or distributed database, and/or associated caches and servers) that store the one or more sets of instructions. The term "machine-accessible storage medium" shall also be taken to include any medium that is capable of storing, encoding or carrying a set of instruction for execution by the machine and that cause the machine to perform any one or more of the methodologies of the present invention. The term "machine-accessible storage medium" shall accordingly be taken to include, but not be limited to, solid-state memories, and optical and magnetic media.

As aforementioned, in one embodiment, the printer engine is represented as and includes modules, components and other features, as described throughout this document. It may also be implemented as discrete hardware components or integrated in the functionality of hardware components such as Application-Specific Integrated Circuit (ASIC), Field-Programmable Gate Array (FPGA), Digital Signal Processor (DSP), etc., or as software or as firmware or functional circuitry.

Throughout the foregoing description, for the purposes of explanation, numerous details are set forth. It will be apparent, however, to one skilled in the art, that the present invention may be practiced without these specific details. In some instances, well-known structures and devices are shown in block diagram form, rather than in detail, in order to avoid obscuring the present invention.

Some portions of the detailed descriptions above are presented in terms of algorithms and symbolic representations of operations on data bits within a computer memory. An algorithm is conceived here to generally be a self-consistent sequence of processes or steps leading to a desired result. These processes or steps are those requiring physical manipulations of physical quantities manifesting as electrical or magnetic signals (e.g., bits, values, elements, symbols, characters, terms, numbers, etc.) capable of being stored, transferred, combined, compared, and otherwise manipulated. Further, terms (such as "accessing", "placing", "analyzing", "communicating", "processing", "compiling", "saving", "storing", "generating", "receiving", "forwarding", "printing", "labeling", "imaging", "directing", "instructing", "displaying", "detecting", etc.) may be associated with various physical quantities and refer to action or processes or steps of processing logic of a processing device, such as the processing device 505, of a data processing device, such as the computer system 500.

It is contemplated that apparatus may be specially constructed for the required purposes, or it may comprise a general purpose computer selectively activated or reconfigured by a computer program stored in the computer. Such a computer program may be stored in a non-transitory machine readable storage medium, such as, but not limited to, any type of disk including floppy disks, optical disks, magnetic-optical disks, ROMs, compact disk ROMs (CD-ROMs), RAMs, erasable programmable ROMs (EPROMs), electrically EPROMs (EEPROMs), magnetic or optical cards, or any type of media suitable for storing electronic instructions, each coupled to a computer system bus. However, it is further contemplated that methods (e.g., algorithms, processes, steps, etc.) and displays presented herein are not inherently related to any particular computer system or apparatus. Various general purpose systems may be used with programs in accordance with the teachings herein, or it may prove convenient to construct more specialized apparatus to perform the required method steps. Moreover, the present invention is not described with reference to any particular programming language or operating system or software platform. For example, it is appreciated that a variety of programming languages may be used to implement the presentation of the invention as described herein.

As aforementioned, embodiments of the present invention may be provided as a computer program product, or software, that may include a non-transitory machine-readable medium having stored thereon instructions, which may be used to program a computer system (or other electronic devices) to perform a process according to the present invention. A machine-readable medium includes any mechanism for storing or transmitting information in a form readable by a machine (e.g., computer system 500). For example, a non-transitory machine-readable 565 (e.g., a non-transitory computer-readable) medium includes a machine (e.g., a computer) readable storage medium (e.g., ROM, RAM, magnetic disk storage media, optical storage media, flash memory devices, etc.), a machine (e.g., computer) readable transmission medium (non-propagating electrical, optical, or acoustical signals), etc.

Many of the methods are described in their most basic form, but processes can be added to or deleted from any of the methods and information can be added or subtracted from any of the described messages without departing from the basic scope of the present invention. It will be apparent to those skilled in the art that many further modifications and adaptations can be made. The particular embodiments are not provided to limit the invention but to illustrate it. The scope of the embodiments of the present invention is not to be determined by the specific examples provided above but only by the claims below.

If it is said that an element "X" is coupled to or with element "Y," element X may be directly coupled to element Y or be indirectly coupled through, for example, element "Z". When the specification or claims state that a component, feature, structure, process, or characteristic X "causes" a component, feature, structure, process, or characteristic Y, it means that "X" is at least a partial cause of "Y" but that there may also be at least one other component, feature, structure, process, or characteristic that assists in causing "Y." If the specification indicates that a component, feature, structure, process, or characteristic "may", "might", or "could" be included, that particular component, feature, structure, process, or characteristic is not required to be included. If the specification or claim refers to "a" or "an" element, this does not mean there is only one of the described elements. Further, an embodiment is an implementation or example of the present invention. Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments.

Any of the above embodiments may be used alone or together with one another in any combination. One or more implementations encompassed within this specification may also include embodiments that are only partially mentioned or alluded to or are not mentioned or alluded to at all in this brief summary or in the abstract. Although various embodiments may have been motivated by various deficiencies with the prior art, which may be discussed or alluded to in one or more places in the specification, the embodiments do not necessarily address any of these deficiencies. In other words, different embodiments may address different deficiencies that may be discussed in the specification. Some embodiments may only partially address some deficiencies or just one deficiency that may be discussed in the specification, and some embodiments may not address any of these deficiencies.

In the foregoing specification, the invention has been described with reference to specific exemplary embodiments thereof. It will, however, be evident that various modifications and changes may be made thereto without departing from the broader spirit and scope of the invention as set forth in the appended claims. The Specification and drawings are, accordingly, to be regarded in an illustrative rather than a restrictive sense.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims, which in themselves recite only those features regarded as the invention.

What is claimed is:

1. A method comprising:
    applying a plurality of coating layers to a glass media to produce a label within a dedicated area of the glass media, wherein the label includes one or more of a human-readable label and a machine-readable label, wherein the plurality of the coating layers include a reflective layer, a photo-sensitive layer, and a seal coating layer, the photo-sensitive layer comprising a photo-sensitive material including photo-sensitive ink that is one or more of light-activated, thermal-activated, and photo-activated, wherein the reflective layer comprises an opaque layer touching the dedicated area, wherein the photosensitive layer is placed on top of the reflective layer, and the seal coating layer is placed on top of the photosensitive layer; and
    generating, using a printing mechanism, an image within the dedicated area of the print media, wherein the image serves as a label and includes a laser-based image.

2. The method of claim 1, wherein the reflective layer is used to reflect a laser light onto the photo-sensitive layer, wherein reflective layer includes a white print area of a media slide or a colored print area of a media cassette,
    wherein the photo-sensitive material is applied via one or more of a sprayer, a roller, and a robotic hand, and
    wherein the chemical-resistant coating layer facilitates protection of the image such that the image is not faded or scratched off by ensuring the photo-sensitive material to be impervious to one or more chemicals being used during laboratory processes within a laboratory environment, wherein the reflective layer is further to produce visible change on the dedicated area from translucent to opaque to form at least one of the human-readable label and the machine-readable label.

3. The method of claim 2, wherein the plurality of coating layers further comprise an opaque layer, wherein the opaque layer is applied to the print media as a colored layer if the print media is made of glass, wherein the colored layer covers the dedicated area where the image is placed.

4. The method of claim 1, wherein the glass media includes at least one of the media cassette, the media slide, a media flask, and a media test tube, wherein the glass media contains laboratory specimen for analytical or evaluative diagnosis, and wherein the glass media further includes a laboratory glassware containment media.

5. The method of claim 1, further comprising locating coordinates of the portion of the surface of the glass media based on the image information.

6. The method of claim 1, wherein the printing mechanism is configured to facilitate printing on the dedicated area of the glass media by revealing the image on the dedicated area including a media coated area of the glass media by creating a chemical bond of the case hardened and formulated chemical compound that becomes visible during a laser timeframe.

7. An apparatus comprising:
    one or more application devices to apply a plurality of coating layers to a glass media to produce a label within a dedicated area of the glass media, wherein the label includes one or more of a human-readable label and a machine-readable label, wherein the plurality of the coating layers include a reflective layer, a photo-sensitive layer, and a seal coating layer, the photo-sensitive layer comprising a photo-sensitive material including photo-sensitive ink that is one or more of light-activated, thermal-activated, and photo-activated, wherein the reflective layer comprises an opaque layer touching the dedicated area, wherein the photosensitive layer is placed on top of the reflective layer, and the seal coating layer is placed on top of the photosensitive layer; and
    a printing mechanism to generate an image within the dedicated area of the print media, wherein the image serves as a label and includes a laser-based image.

8. The apparatus of claim 7, wherein the reflective layer is used to reflect a laser light onto the photo-sensitive layer, wherein reflective layer includes a white print area of a media slide or a colored print area of a media cassette, wherein the photo-sensitive material is applied via one or more of a sprayer, a roller, and a robotic hand, and wherein the chemical-resistant coating layer facilitates protection of the image such that the image is not faded or scratched off by ensuring the photo-sensitive material to be impervious to one or more chemicals being used during laboratory processes within a laboratory environment, wherein the reflective layer is further to produce visible change on the dedicated area from translucent to opaque to form at least one of the human-readable label and the machine-readable label.

9. The apparatus of claim 8, wherein the plurality of coating layers further comprise an opaque layer, wherein the opaque layer is applied to the print media as a colored layer if the print media is made of glass, wherein the colored layer covers the dedicated area where the image is placed.

10. The apparatus of claim 7, wherein the glass media includes at least one of the media cassette, the media slide, a media flask, and a media test tube, wherein the glass media contains laboratory specimen for analytical or evaluative diagnosis, and wherein the glass media further includes a laboratory glassware containment media.

11. The apparatus of claim 7, further comprising locating coordinates of the portion of the surface of the glass media based on the image information.

12. The apparatus of claim 7, wherein the printing mechanism is configured to facilitate printing on the dedicated area of the glass media by revealing the image on the dedicated area including a media coated area of the glass media by creating a chemical bond of the case hardened and formulated chemical compound that becomes visible during a laser timeframe.

13. The apparatus of claim 7, further comprising:
a laser source having a variable or fixed frequency laser device of variable or fixed power;
a glass media of a plurality of glass medium, wherein a variable or fixed length focal distance is placed between one or more of the laser source, a reflective device, and a media surface of the glass media; and
a system controller to control reflections of laser emissions from the laser source and the media surface of the glass media, wherein the system controller is further coupled to the laser source, wherein the system controller is further to control laser power and modulation emissions from the laser source.

14. The apparatus of claim 7, wherein the system controller is further to store and virtualize one or more of the glass media, a dedicated surface area of the glass media where an image is placed, a type of the glass media, and one or more other types of the plurality of glass medium to be imaged, wherein the system controller is further to control the laser source to form images that are consistent with one or more of varying sizes, shapes, types, and locations of the plurality of glass medium, wherein the system controller is further to virtualize each image to be formed within a memory based on positioning of each of the plurality of glass medium, wherein the system controller is further to move the multi axis reflective device in a variety of axis to form each image consistent with multi-dimensional glass media surfaces of the plurality of glass medium, and wherein the system controller is further to configure the laser source to change relevant output parameters to create a monochromatic or grey scale image consistent with the multi-dimensional glass media surfaces of the plurality of glass medium.

15. At least one non-transitory machine-readable medium having stored thereon instructions that when executed by a computing device, cause the computing device to perform one or more operations comprising:

applying a plurality of coating layers to a glass media to produce a label within a dedicated area of the glass media, wherein the label includes one or more of a human-readable label and a machine-readable label, wherein the plurality of the coating layers include a reflective layer, a photo-sensitive layer, and a seal coating layer, the photo-sensitive layer comprising a photo-sensitive material including photo-sensitive ink that is one or more of light-activated, thermal-activated, and photo-activated, wherein the reflective layer comprises an opaque layer touching the dedicated area, wherein the photosensitive layer is placed on to of the reflective layer, and the seal coating layer is placed on to of the photosensitive layer; and generating, using a printing mechanism, an image within the dedicated area of the print media, wherein the image serves as a label and includes a laser-based image.

16. The non-transitory machine-readable medium of claim 15, wherein the reflective layer is used to reflect a laser light onto the photo-sensitive layer, wherein reflective layer includes a white print area of a media slide or a colored print area of a media cassette, wherein the photo-sensitive material is applied via one or more of a sprayer, a roller, and a robotic hand, and wherein the chemical-resistant coating layer facilitates protection of the image such that the image is not faded or scratched off by ensuring the photo-sensitive material to be impervious to one or more chemicals being used during laboratory processes within a laboratory environment, wherein the reflective layer is further to produce visible change on the dedicated area from translucent to opaque to form at least one of the human-readable label and the machine-readable label.

17. The non-transitory machine-readable medium of claim 16, wherein the plurality of coating layers further comprise an opaque layer, wherein the opaque layer is applied to the print media as a colored layer if the print media is made of glass, wherein the colored layer covers the dedicated area where the image is placed.

18. The non-transitory machine-readable medium of claim 15, wherein the glass media includes at least one of the media cassette, the media slide, a media flask, and a media test tube, wherein the glass media contains laboratory specimen for analytical or evaluative diagnosis, and wherein the glass media further includes a laboratory glassware containment media.

19. The non-transitory machine-readable medium of claim 15, further comprising locating coordinates of the portion of the surface of the glass media based on the image information.

20. The non-transitory machine-readable medium of claim 15, wherein the printing mechanism is configured to facilitate printing on the dedicated area of the glass media by revealing the image on the dedicated area including a media coated area of the glass media by creating a chemical bond of the case hardened and formulated chemical compound that becomes visible during a laser timeframe.

* * * * *

UNITED STATES PATENT AND TRADEMARK OFFICE
CERTIFICATE OF CORRECTION

PATENT NO. : 8,951,614 B2  
APPLICATION NO. : 13/092728  
DATED : February 10, 2015  
INVENTOR(S) : Collins et al.

It is certified that error appears in the above-identified patent and that said Letters Patent is hereby corrected as shown below:

In the claims

In column 13 at line 60 delete, "... move the multi axis reflective device in a variety of axis to ...".

In column 14 at line 19 delete, "photosensitive layer is placed on to of the reflective ...", and insert --photosensitive layer is placed on top of the reflective--.

In column 14 at line 20 delete, "layer, and the seal coating layer is placed on to of the ...", and insert --layer, and the seal coating layer is placed on top of the--.

Signed and Sealed this  
Third Day of May, 2016

Michelle K. Lee  
*Director of the United States Patent and Trademark Office*